(12) United States Patent
Lutz

(10) Patent No.: US 10,610,276 B2
(45) Date of Patent: Apr. 7, 2020

(54) SCREW

(71) Applicant: Bluewater Medical GmbH, Kiel (DE)

(72) Inventor: Christian Lutz, Heikendorf (DE)

(73) Assignee: Bluewater Medical GmbH, Kiel (DE)

( * ) Notice: Subject to any disclaimer, the term of this patent is extended or adjusted under 35 U.S.C. 154(b) by 103 days.

(21) Appl. No.: 15/724,345

(22) Filed: Oct. 4, 2017

(65) Prior Publication Data

US 2018/0092681 A1 Apr. 5, 2018

(30) Foreign Application Priority Data

Oct. 5, 2016 (DE) .................. 10 2016 011 947

(51) Int. Cl.
*A61B 17/86* (2006.01)
*F16B 31/04* (2006.01)
*A61B 17/88* (2006.01)
*A61B 17/00* (2006.01)

(52) U.S. Cl.
CPC ........ *A61B 17/8685* (2013.01); *A61B 17/863* (2013.01); *A61B 17/864* (2013.01); *A61B 17/8869* (2013.01); *A61B 2017/00862* (2013.01); *F16B 31/04* (2013.01); *Y10S 411/916* (2013.01)

(58) Field of Classification Search
CPC ......... A61F 2002/0829; Y10S 411/916; A61B 17/8685; A61B 17/864; A61B 17/869; A61B 17/8869; A61B 17/86; A61B 2017/00862; F16B 31/04; F16B 35/041
USPC .......................................... 411/392
See application file for complete search history.

(56) References Cited

U.S. PATENT DOCUMENTS

| | | | | | |
|---|---|---|---|---|---|
| 4,854,797 | A | * | 8/1989 | Gourd | F16B 33/006 411/383 |
| 4,947,502 | A | * | 8/1990 | Engelhardt | A61B 17/86 411/392 |
| 4,959,064 | A | | 9/1990 | Engelhardt | |
| 5,061,137 | A | * | 10/1991 | Gourd | F16B 19/00 411/392 |
| 5,102,276 | A | * | 4/1992 | Gourd | F16B 33/006 411/383 |
| 5,312,255 | A | * | 5/1994 | Bauer | A61C 8/0012 433/173 |
| 7,547,324 | B2 | * | 6/2009 | Cragg | A61B 17/70 623/17.11 |

(Continued)

FOREIGN PATENT DOCUMENTS

| | | |
|---|---|---|
| CA | 2 391 115 A1 | 12/2002 |
| EP | 1 273 269 A2 | 1/2003 |

(Continued)

*Primary Examiner* — David W Bates
(74) *Attorney, Agent, or Firm* — Collard & Roe, PC

(57) ABSTRACT

A screw includes a head part, a threaded part and a flexible connector between the head part and the threaded part for transmitting a torsional force between the head part and the threaded part, and to allow two bending movements between the head part and the threaded part in opposite directions in the longitudinal axis of the screw. The head part and the threaded part in each case have a longitudinal axis, which can be arranged offset in parallel to one another. The screw has an ε-modulus of between 20,000 and 100,000 N/mm² against a rotation in the case of an arrangement of the head part and the threaded part on a longitudinal axis.

15 Claims, 3 Drawing Sheets

(56) References Cited

U.S. PATENT DOCUMENTS

| | | | | |
|---|---|---|---|---|
| 7,955,388 B2* | 6/2011 | Jensen | A61B 17/68 | 606/323 |
| 8,048,134 B2* | 11/2011 | Partin | A61B 17/7225 | 606/301 |
| 8,114,124 B2* | 2/2012 | Buckman | A61B 17/08 | 606/213 |
| 8,197,523 B2* | 6/2012 | Bottlang | A61B 17/8605 | 606/301 |
| 8,491,637 B2* | 7/2013 | Matthis | A61B 17/702 | 606/254 |
| 8,529,611 B2* | 9/2013 | Champagne | A61B 17/7225 | 606/328 |
| 8,585,338 B2* | 11/2013 | Wernersson | E04B 9/18 | 248/330.1 |
| 8,597,337 B2* | 12/2013 | Champagne | A61B 17/863 | 606/309 |
| 8,828,067 B2* | 9/2014 | Tipirneni | A61B 17/742 | 606/320 |
| 9,241,806 B2* | 1/2016 | Suh | A61B 17/8625 | |
| 9,339,316 B2* | 5/2016 | Hulliger | A61B 17/84 | |
| 9,498,264 B2* | 11/2016 | Harshman | A61B 17/7208 | |
| 2002/0198527 A1* | 12/2002 | Muckter | A61B 17/866 | 606/316 |
| 2005/0240198 A1* | 10/2005 | Albertson | A61B 17/8076 | 606/103 |
| 2005/0277940 A1* | 12/2005 | Neff | A61B 17/7225 | 606/916 |
| 2006/0264954 A1* | 11/2006 | Sweeney, II | A61B 17/8685 | 606/312 |
| 2007/0282342 A1 | 12/2007 | Niederberger et al. | | |
| 2009/0062868 A1* | 3/2009 | Casutt | A61B 17/7001 | 606/316 |
| 2009/0157123 A1* | 6/2009 | Appenzeller | A61B 17/68 | 606/301 |
| 2009/0198287 A1* | 8/2009 | Chiu | A61B 17/863 | 606/301 |
| 2009/0198289 A1* | 8/2009 | Manderson | A61B 17/864 | 606/304 |
| 2011/0087294 A1* | 4/2011 | Reiley | A61B 17/1659 | 606/279 |
| 2011/0257689 A1* | 10/2011 | Fiechter | A61B 17/866 | 606/301 |
| 2011/0282387 A1* | 11/2011 | Suh | A61B 17/70 | 606/246 |
| 2011/0295252 A1* | 12/2011 | Tipirneni | A61B 17/683 | 606/62 |
| 2012/0101534 A1 | 4/2012 | Pitbladdo | | |
| 2012/0172936 A1* | 7/2012 | Horrell | A61B 17/0401 | 606/319 |
| 2013/0131733 A1 | 5/2013 | Chien et al. | | |
| 2014/0163624 A1* | 6/2014 | Siegal | A61B 17/7032 | 606/304 |
| 2015/0012048 A1* | 1/2015 | Huebner | A61B 17/864 | 606/304 |
| 2015/0320464 A1* | 11/2015 | Schmidt | A61B 17/888 | 606/304 |
| 2015/0342656 A1* | 12/2015 | Bertollo | A61B 17/8685 | 606/304 |
| 2015/0374418 A1* | 12/2015 | Martin | A61B 17/1671 | 606/291 |
| 2016/0038201 A1* | 2/2016 | Cummings | A61B 17/866 | 606/304 |
| 2016/0235447 A1 | 8/2016 | Mundis, Jr. et al. | | |
| 2016/0287302 A1* | 10/2016 | Horrell | A61B 17/84 | |
| 2017/0079699 A1* | 3/2017 | Fallin | A61B 17/1725 | |
| 2017/0258572 A1* | 9/2017 | Gordon | A61F 2/0811 | |
| 2018/0221072 A1* | 8/2018 | P | A61F 2/28 | |
| 2018/0263669 A1* | 9/2018 | Peterson | A61B 17/8695 | |
| 2018/0344374 A1* | 12/2018 | Summitt | A61B 17/8625 | |
| 2019/0090926 A1* | 3/2019 | Lutz | A61B 17/8875 | |
| 2019/0209220 A1* | 7/2019 | Lee | A61B 17/846 | |
| 2019/0336190 A1* | 11/2019 | Allard | A61F 2/0805 | |
| 2019/0336270 A1* | 11/2019 | Dacosta | A61B 17/864 | |

FOREIGN PATENT DOCUMENTS

| | | |
|---|---|---|
| EP | 1 753 355 B1 | 11/2011 |
| WO | 2006/105935 A1 | 10/2006 |

* cited by examiner

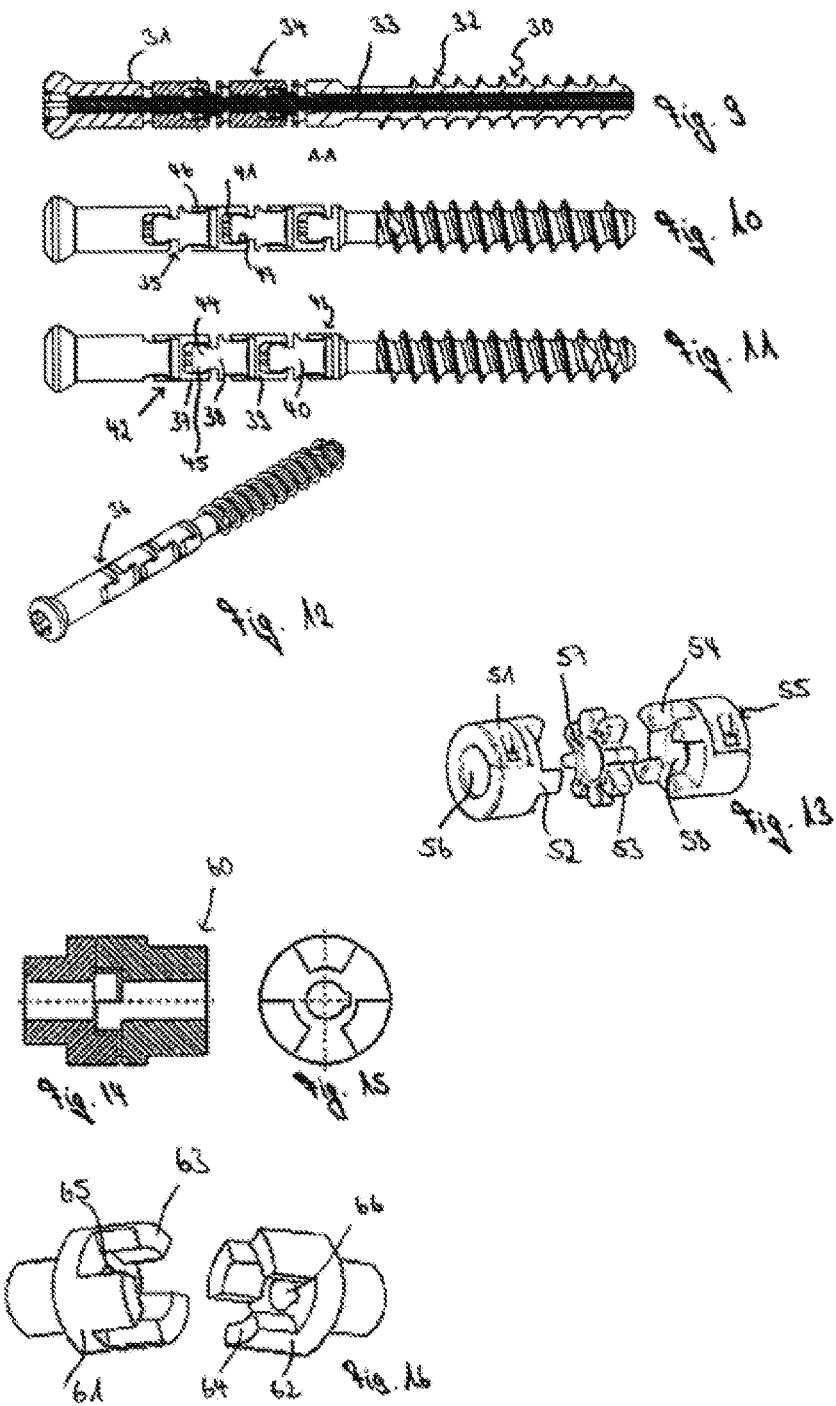

SCREW

CROSS REFERENCE TO RELATED APPLICATIONS

Applicant claims priority under 35 U.S.C. § 119 of German Application No. 10 2016 011 947.0 filed Oct. 5, 2016, the disclosure of which is incorporated by reference.

BACKGROUND OF THE INVENTION

1. Field of the Invention

The invention relates to a screw comprising a head part, a threaded part and a flexible connector between head part and threaded part. The fixation of two bones at a fixed distance to one another, while simultaneously maintaining the mobility of the bones to one another, for example for bridging a joint gap, is the object of the screw. The demand on the screw is to be able to absorb tensile forces, which are as high as possible, and to thereby simultaneously offer the least possible resistance to a displacement of the bones (at right angles to the tensile direction) and to thereby be able to develop a sufficiently high torque to be able to be screwed into the bone and also out of the bone again.

2. Description of the Related Art

Such a screw is known from EP-A-1 273 269 MÜCKTER. Here, the flexible connector between head part and threaded part is formed by means of a wire rope, a string, a bundle of wire or through threads. The bundle of wire can be reinforced by a sheath or a coil pulled over from outside. In response to the implantation of such a screw, the threaded part is initially screwed into the bone by means of a bone thread in terms of a stud bolt. This is carried out by means of a cannulated socket key, which is pushed over the wire rope or the bundle of wire or the strings, respectively, or the bolt, and which engages with the threaded part on the hexagon head. Using a cannulated hexagon socket screw key, a hexagon socket head nut is then screwed onto the bolt with metal thread. Finally, the wire rope or bundle of wire protruding on the hexagon socket is shortened by means of a pair of nippers. Even though the elastic joint provides the screw with a certain axial elasticity, a transmission of torques is not possible without using the special socket key.

A bone screw comprising a spring member is known from U.S. Pat. No. 4,959,064. The spring member in the shaft of the bone screw provides the bone with a certain axial elasticity (axial compression or distraction). A bending is possible, but a transmission of a torque is not.

EP-A-1 753 355 B1 NIEDERBERGER describes the transmission of a torque from the head part to the threaded part while maintaining a flexible joint. The flexibility between head part and threaded part is attained by means of a ball joint, in the case of which the head part has a ball socket and the threaded part has a ball head. For the transmission of a torque, the ball head has an octagonal cross section and the ball socket has a correspondingly adapted, octagonal geometry, which is suitable to accommodate the ball head. A rotation of the bone screw is thus also attained in the angled state. A universal or cardan joint is also mentioned as alternative.

The ball joint comprising octagonal head has the result that the eight corners round on the ball head in response to larger toques, and the ball joint widens. Only small torques can thus be transmitted. In the case of a universal joint, the filigree universal joint is not possible for the transmission of larger torques and tensile forces with small shaft diameters.

In one embodiment, WO 2006 105935 A1 allows only one bending movement and even though the other exemplary embodiments allow for a plurality of bending movements, the screw is then so elastic in its longitudinal extension that it does not make it possible any longer to be able to accurately maintain the distance of the bones relative to one another and to transmit a torque from the head part to the threaded part.

In the case of all embodiments, the possibility of an offset between head part and threaded part is gained with an inaccurate transmission of the torque between head part and threaded part.

SUMMARY OF THE INVENTION

The invention is thus based on the object of further developing such screws in such a way that it is suitable for a use for bridging bone parts located at a distance from one another and supports or even completely takes over the stabilization, which is at hand in the body, for example by means of ligaments.

In the case of a generic screw, this object is solved by means of the features of described herein. The transmission of particularly high tensile forces in the case of a limited shaft diameter opens up a plurality of fields of application for such a screw.

Advantageous further developments are also described. The constructional design is thereby significant for the invention, even without the feature of elasticity.

The invention is based on the knowledge that it is expedient to provide different constructional designs for the transmission of tensile forces and torques. To provide these designs, which are in each case optimized for two different functions, at a generic screw, coupling and flexible joint are arranged concentrically to one another. This makes it possible to use and to optimize the flexible joints, which are known from the prior art, such as in particular from EP-A 1 273 269 MÜCKTER, and, on the other hand, to provide for a coupling, which is optimized for the transmission of a torque. The concentric arrangement ensures a compact setup in the joint area.

As a core, the coupling can be arranged in the center of the joint area or around a cannulation. The flexible joint is then provided radially outside of the coupling. It is advantageous, however, to arrange the coupling around the flexible joint. In particular in the case of wire ropes, strings, a bundle of wire or threads, they can be guided inside the coupling and can be held together by means of the coupling. A rod or tube can also be guided and held easily inside the coupling to absorb the axial forces and to provide a flexible joint between head part and threaded part. The torsional forces can then substantially be absorbed by the coupling.

It is thus proposed for the flexible joint part to absorb the tensile forces in response to a tension between head part and threaded part, and for the coupling to absorb the torsional forces in response to a torsion between head part and threaded part.

The constructional design makes it possible to use a rope, a cord or a chain, for example, as flexible joint.

With regard to the connection between joint part and head part or threaded part, it is proposed for at least a portion of the flexible joint part to be arranged in the head part or in the threaded part, respectively. This provides for a connection by means of welding, soldering, shrinking or crimping within the head part or from the threaded part.

To attain a particularly compact setup, it is proposed for the coupling to be positively connected to head part and threaded part. This makes it possible to already obtain a certain flexibility at the joint location between head part and threaded part.

The coupling preferably has a plurality of elements, which are positively connected to one another. This makes it possible to change the flexibility and the length of the flexible joint part in a simple manner by means of the number of elements. The elements thereby preferably have the same shape or two elements of different shapes alternate.

A preferred embodiment provides for the coupling, as positive connection, to have a groove and tongue joint. Provision can thereby be made offset to one another on annular elements for grooves and tongues, so that groove and tongue engage with one another when a plurality of such annular elements are arranged one behind the other.

It is particularly preferred to provide a dovetail joint as positive connection on the coupling. As a result, the individual coupling elements cannot be pulled apart in the axial direction. By threading onto a flexible joint part, the elements can even be arranged in an undetachable manner. It is thus proposed for the coupling to have a plurality of annular elements, which are preferably threaded onto the flexible joint part.

The head part can have a threadless shaft and/or a thread. According to the known operating principle of the HERBERT screw, the thread on the head part can have a larger diameter as compared to the threaded part and a smaller thread pitch. When screwing this screw into a broken bone vertically to the fracture plane, the two fragments are moved towards one another and are braced again one another, whereby the extent of being moved towards one another for each screw rotation follows from the difference of the two thread pitches.

Independent of the embodiment of the head part, it is advantageous, when the maximum diameter of flexible joint part and coupling, which are arranged concentrically to one another, is not larger than and preferably even smaller than the maximum outer diameter of the threaded part.

Such screws are suitable for a large variety of purposes. A particularly relevant field of application lies in the field of medical technology. It is thus proposed for the screw to be a bone screw.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings,

FIG. 9 shows a section through a screw with larger angular play, FIG. 12 shows a three-dimensional view of the screw shown in FIG. 9, FIG. 13 shows a coupling element with star body, FIG. 14 shows a section through two coupling elements, which cooperate in a positive manner by means of claws, FIG. 15 shows a view of a coupling element according to FIG. 14, FIG. 16 shows a three-dimensional view of two cooperating coupling elements according to FIG. 14, FIG. 17 shows a screw according to FIGS. 9 to 12 in an orientation with head part, which is arranged offset parallel to the threaded part, and FIG. 18 shows the screw shown in FIG. 17, inserted between fibula and tibia.

DETAILED DESCRIPTION OF PREFERRED EMBODIMENTS

Figure 1:
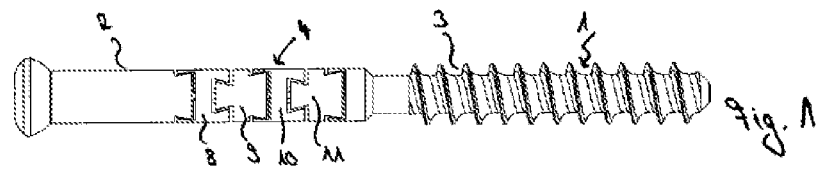
FIG. 1 shows a view of a screw comprising dovetail toothing.

The screw 1 shown in FIG. 1 has a head part 2 and a threaded part 3. As flexible joint part 4, provision is made between the head part 2 and the threaded part 3 for a combination of a first coupling element 5 with a plug-in connector 6 for transmitting torsional forces, and a second coupling element 7 for transmitting tensile forces. In the axial direction between head part 2 and threaded part 3, the first coupling element 5 of the flexible joint part 4 consists of 4 joint elements 8, 9, 10 and 11, which are arranged one behind the other.

Figure 2:
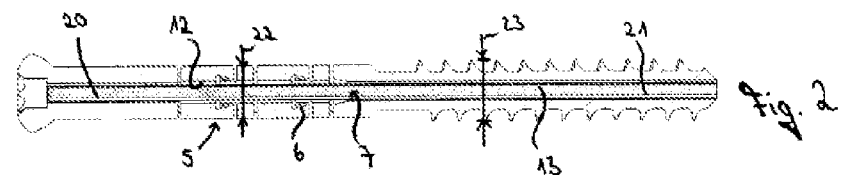
FIG. 2 shows a section through the screw shown in FIG. 1.
Figure 3:
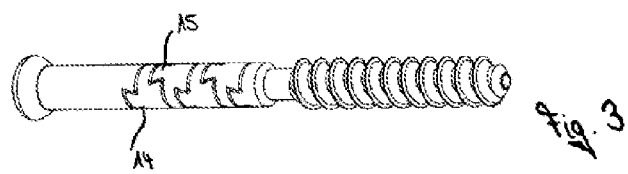
FIG. 3 shows a perspective view of the screw shown in FIG. 1.
Figure 4:
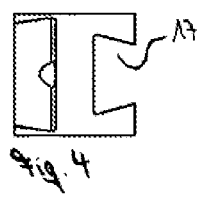
FIGS. 4-7 show different views of a coupling element of the screw shown in FIG. 1.
Figure 5:
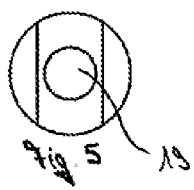
Figure 8:
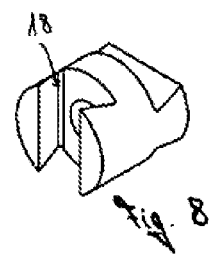
FIG. 8 shows a perspective view of the coupling element of the screw shown in FIG. 1.
Figure 6:
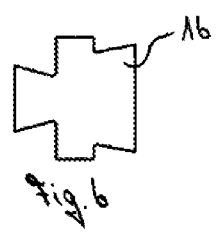
Figure 7:
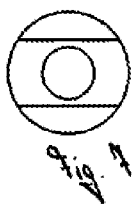
Figure 10:
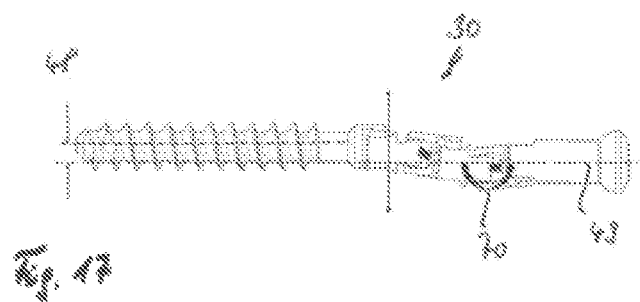
FIG. 10 shows a first side view of the screw shown in FIG. 9.
Figure 11:
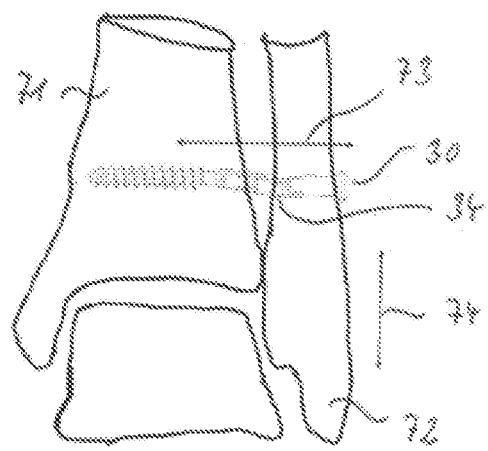
FIG. 11 shows a second side view of the screw shown in FIG. 9.

The first coupling element 5 with the joint elements 8 to 11 has a central bore 12, which makes it possible to arrange a flexible wire inside the first coupling element 5 as second coupling element 7. This wire 13 is fixedly connected to the head part 2 and the threaded part 3 and thus allows the transmission of tensile forces between head part 2 and threaded part 3, while the wire only offers a very small resistance to torsional forces. The torsional forces are transmitted via the first coupling element 5 from the head part to the threaded part via a positive connection 14. For this purpose, the screw 1 is provided with a groove and tongue joint 15. In the case of this groove and tongue joint, the tongue 16 is arranged in the groove 17 with an axial play of approximately 0.1 mm. In the case at hand, the play between the five joint elements, the head part and the threaded part at the five contact surfaces adds up to approximately 0.7 mm. This provides for a certain angular play around the longitudinal axis of the screw 1. For this purpose, the joint elements 8 to 11 are embodied annularly with a dovetail joint 18, which can be inserted into one another at right angles to the longitudinal axis of the screw, and which are secured against being detached and being displaced after being threaded onto the wire 13 of the second coupling element 7. For this purpose, the individual annular joint elements in each case have a bore 19, in which a rope, a cord, a chain, a tube, a rod or a coil can be arranged instead of the flexible wire shown in FIG. 2 as second coupling element 7, provided that these elements are suitable to allow a certain torsional force and to absorb a tensile force.

To fasten the second coupling element 7 in the head part 2, the first end 20 is arranged in the head part 2 and is welded at that location, while the second end 21 of the second coupling element 7 is welded in the threaded part 3.

The maximum diameter 22 of the coupling elements 8 to 11 is slightly smaller than the maximum diameter 23 of the threaded part 3.

The screw 30 shown in FIGS. 9 to 12 is made of a head part 31, a threaded part 32 and a flexible joint part 33, substantially like the screw 1. However, the screw 30 differs from the screw 1 by the formation of the flexible joint part 34. The first coupling element 35 has four joint elements 37, 38, 39 and 40, which are connected to one another and to the head part 31 and the threaded part 32 via a plug-in connection 36. The wire runs as second coupling element 41 inside these joint elements 37 to 40.

The screw 30 has a special groove and tongue joint 43 as positive connection 42, in the case of which a head part 44 has convex contact surfaces 45 in one view and concave contact surfaces 46 in a vertical view. The contact surfaces cooperate with correspondingly formed contact surfaces of an accommodation 47, which is arranged on the same joint element.

The special embodiment of the joint elements provides for a larger angular play around the longitudinal axis of the screw 30.

Provision can also be made for other positive connections in addition to the dovetail joint 18 provided in the case of the screw 1 and the special groove tongue joint 34 provided on the screw 30. FIG. 13 shows for example a three-part joint element 50 of a first holding part 51, which cooperates with claws 52 with a star-shaped central part 53, while the star-shaped central part 53 also cooperates with claws 54 of a second holding part 55. The holding parts 51 and 55 as well as the star-shaped central part 53 have central bores 56, 57 and 58, in which a flexible joint part (not shown) can be guided.

FIGS. 14 to 16 show a two-part coupling element 60, in the case of which joint elements 61 and 62 cooperate via claws 63 and 64, while both joint elements in each case have a central bore 65 and 66, in which a second coupling element (not shown) can be guided.

FIG. 17 shows the screw 30 shown in FIGS. 9 to 12 with a threaded part 32, which is arranged on a longitudinal axis 48, while the head part 31 is arranged on a longitudinal axis 49, which is located offset parallel thereto. In response to a rotation according to the arrow 70, the threaded part 32 rotates without play and without perceivable elasticity with the head part 31.

The screw 30 can thus be inserted for example between the tibia 71 and the fibula 72, in order to hold the fibula 72 against high forces acting in the Z-direction 73, while the flexible joint part 34 allows for a very high flexibility in the X- and Y-direction 74, in order to provide for a natural movement of the joint. The Z-direction thereby extends in the longitudinal axis of the screw, and the X- and Y-direction extend orthogonally thereto.

Although only a few embodiments of the present invention have been shown and described, it is to be understood that many changes and modifications may be made thereunto without departing from the spirit and scope of the invention.

The invention claimed is:

1. A screw comprising a head part, a threaded part, and a flexible connector between the head part and the threaded part for transmitting a torsional force between the head part and the threaded part, and to allow two bending movements between the head part and the threaded part, wherein the head part has a head part longitudinal axis and the threaded part has a threaded part longitudinal axis, which can be arranged offset in parallel to one another with an offset, wherein the flexible connector has a first coupling element comprising at least two joint elements to transmit torsional forces among the at least two joint elements, and has a second coupling element fixedly connected to the head part and to the threaded part such that the second coupling element transmits tensional forces from the head part to the threaded part, wherein the first coupling element and the second coupling element are arranged concentrically to one another, and wherein the second coupling element is a rope, a cord or a chain and extends along a central longitudinal axis of the screw.

2. The screw according to claim 1, wherein the offset is at least 0.3 mm per 6 mm length of the flexible connector between the head part longitudinal axis and the threaded part longitudinal axis of the threaded part, which is parallel thereto, in the area of the flexible connector.

3. The screw according to claim 1, wherein the at least two joint elements are one behind the other in a direction of the central longitudinal axis and between the head part and the threaded part.

4. The screw according to claim 1, wherein the first coupling element is arranged around the second coupling element.

5. The screw according to claim 1, wherein the first coupling element has a groove and tongue joint as a positive connection.

6. The screw according to claim 1, wherein the first coupling element has a dovetail joint as a positive connection.

7. The screw according to claim 1, wherein the at least two joint elements comprise annular joint elements.

8. The screw according to claim 7, wherein the annular joint elements are threaded onto the second coupling element.

9. The screw according to claim 1, wherein the second coupling element is only a single element comprising only one central longitudinal axis of extension.

10. The screw according to claim 1, wherein at the diameter of the second coupling element is between 0.5 and 5 mm.

11. The screw according to claim 1, wherein at least a first end of the second coupling element is arranged in the head part.

12. The screw according to claim 1, wherein at least a second end of the second coupling element is arranged in the threaded part.

13. The screw according to claim 1, wherein the maximum diameter of the at least two joint elements is not larger than the maximum outer diameter of the threaded part.

14. The screw according to claim 1, wherein the diameter of the at least two joint elements is between 2.0 mm and 8.5 mm.

15. The screw according to claim 1, wherein the screw is a bone screw.

* * * * *

UNITED STATES PATENT AND TRADEMARK OFFICE
CERTIFICATE OF CORRECTION

PATENT NO. : 10,610,276 B2
APPLICATION NO. : 15/724345
DATED : April 7, 2020
INVENTOR(S) : Lutz Page 1 of 1

It is certified that error appears in the above-identified patent and that said Letters Patent is hereby corrected as shown below:

In Claim 10, Column 6, Line 46, after "wherein" please delete "at".

Signed and Sealed this
Twenty-third Day of June, 2020

Andrei Iancu
*Director of the United States Patent and Trademark Office*